United States Patent
Collias et al.

(10) Patent No.: US 9,862,670 B2
(45) Date of Patent: Jan. 9, 2018

(54) BI-COMPONENT CATALYST AND METHOD FOR DEHYDRATING LACTIC ACID TO ACRYLIC ACID

(71) Applicant: The Procter & Gamble Company, Cincinnati, OH (US)

(72) Inventors: Dimitris Ioannis Collias, Mason, OH (US); Jeffrey Charles Hayes, West Chester, OH (US); William David Laidig, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/067,211

(22) Filed: Mar. 11, 2016

(65) Prior Publication Data

US 2016/0264505 A1    Sep. 15, 2016

Related U.S. Application Data

(60) Provisional application No. 62/132,541, filed on Mar. 13, 2015.

(51) Int. Cl.
 *C07C 51/347* (2006.01)
 *C07C 51/377* (2006.01)
 *B01J 23/00* (2006.01)
 *B01J 23/20* (2006.01)

(52) U.S. Cl.
 CPC ............. *C07C 51/347* (2013.01); *B01J 23/00* (2013.01); *B01J 23/20* (2013.01); *C07C 51/377* (2013.01)

(58) Field of Classification Search
 CPC .......... B01J 23/00; B01J 23/20; C07C 51/347; C07C 51/377
 See application file for complete search history.

(56) References Cited

U.S. PATENT DOCUMENTS

| 3,770,837 A | * | 11/1973 | Favstritsky | ........... C07C 29/149 568/814 |
|---|---|---|---|---|
| 5,071,754 A | | 12/1991 | Walkup et al. | |
| 2013/0274517 A1 | | 10/2013 | Godlewski et al. | |

FOREIGN PATENT DOCUMENTS

WO    WO2008049440 A1    5/2008

OTHER PUBLICATIONS

International Search Report and Written Opinion (PCT/US2016/020665) dated May 24, 2016.
Korstanje, J.J.: "Rhenium- and molybdenum-catalyzed dehydration reactions. A fundamental step in the conversion of bio-based alcohols to olefins", URL:http://dspace.library.uu.nl/handle/1874/273464, p. 138, table 1, retrieved on May 11, 2016.
TIES&EMSP14;J.. Korstanje et al:, "Catalytic Dehydration of Benzylic Alcohols to Styrenes by Rhenium Complexes", Chemsuschem, vol. 3, No. 6, Jun. 21, 2010, pp. 695-697.

* cited by examiner

*Primary Examiner* — Pancham Bakshi
*Assistant Examiner* — Mark Luderer
(74) *Attorney, Agent, or Firm* — Brent M. Peebles

(57) ABSTRACT

Bicomponent catalysts and methods for making bio-based acrylic acid, acrylic acid derivatives, or mixtures thereof from lactic acid, lactic acid derivatives, or mixtures thereof are provided.

15 Claims, No Drawings

BI-COMPONENT CATALYST AND METHOD FOR DEHYDRATING LACTIC ACID TO ACRYLIC ACID

FIELD OF THE INVENTION

The present invention generally relates to bicomponent catalysts and methods for producing bio-based acrylic acid, acrylic acid derivatives, or mixtures thereof. More specifically, the method includes contacting a stream of lactic acid, lactic acid derivatives, or mixtures thereof with a bicomponent catalyst, which comprises an HO—Re(VII)=O moiety and a compound having an oxophilic metal. In one embodiment, the oxophilic metal compound comprises a Nb or Ta oxide.

BACKGROUND OF THE INVENTION

Acrylic acid, acrylic acid derivatives, or mixtures thereof have a variety of industrial uses, typically consumed in the form of polymers. In turn, these polymers are commonly used in the manufacture of, among other things, adhesives, binders, coatings, paints, polishes, detergents, flocculants, dispersants, thixotropic agents, sequestrants, and superabsorbent polymers (SAP), which are used in disposable absorbent articles, including diapers and hygienic products, for example. Acrylic acid is commonly made from fossil resources. For example, acrylic acid has long been prepared by catalytic oxidation of propylene. These and other methods of making acrylic acid from fossil sources are described in the Kirk-Othmer Encyclopedia of Chemical Technology, Vol. 1, pgs. 342-369 (5$^{th}$ Ed., John Wiley & Sons, Inc., 2004). Fossil-derived acrylic acid contributes to greenhouse emissions due to its high fossil-derived carbon content. Furthermore, fossil resources are not renewable materials, as it takes hundreds of thousands of years to form naturally and only a short time to consume. As fossil resources become increasingly scarce, more expensive, and subject to regulations for $CO_2$ emissions, there exists a growing need for bio-based acrylic acid, acrylic acid derivatives, or mixtures thereof that can serve as an alternative to fossil-derived acrylic acid, acrylic acid derivatives, or mixtures thereof.

Many attempts have been made over the last 80 years to make bio-based acrylic acid, acrylic acid derivatives, or mixtures thereof from non-fossil sources, such as lactic acid (also known as 2-hydroxypropionic acid), lactic acid derivatives (e.g. alkyl 2-acetoxy-propionate and 2-acetoxy propionic acid), 3-hydroxypropionic acid, glycerin, carbon monoxide and ethylene oxide, carbon dioxide and ethylene, and crotonic acid. From these non-fossil sources, only lactic acid is produced today in high yield from sugar (≥90% of theoretical yield, or equivalently, ≥0.9 g of lactic acid per g of sugar) and purity, and economics which could support producing acrylic acid at a cost competitive to fossil-derived acrylic acid. As such, lactic acid or lactate presents a real opportunity of serving as a feedstock for bio-based acrylic acid, acrylic acid derivatives, or mixtures thereof. Also, 3-hydroxypropionic acid is expected to be produced at commercial scale in a few years, and as such, 3-hydropropionic acid will present another real opportunity of serving as feedstock for bio-based acrylic acid, acrylic acid derivatives, or mixtures thereof. Sulfate salts; phosphate salts; mixtures of sulfate and phosphate salts; bases; zeolites or modified zeolites; metal oxides or modified metal oxides; and supercritical water are the main catalysts which have been used to dehydrate lactic acid or lactate to acrylic acid, acrylic acid derivatives, or mixtures thereof in the past with varying success.

For example, U.S. Pat. No. 4,786,756 (issued in 1988), describes the vapor phase dehydration of lactic acid or ammonium lactate to acrylic acid using aluminum phosphate ($AlPO_4$) treated with an aqueous inorganic base as a catalyst. As an example, the '756 patent discloses a maximum yield of acrylic acid of 43.3% when lactic acid was fed into the reactor at approximately atmospheric pressure, and a respective yield of 61.1% when ammonium lactate was fed into the reactor. In both examples, acetaldehyde was produced at yields of 34.7% and 11.9%, respectively, and other side products were also present in large quantities, such as propionic acid, CO, and $CO_2$. Omission of the base treatment caused increased amounts of the side products. Another example is Hong et al., Appl. Catal. A: General 396:194-200 (2011), who developed and tested composite catalysts made with $Ca_3(PO_4)_2$ and $Ca_2(P_2O_7)$ salts with a slurry-mixing method. The catalyst with the highest yield of acrylic acid from methyl lactate was the 50%-50% (by weight) catalyst. It yielded 68% acrylic acid, about 5% methyl acrylate, and about 14% acetaldehyde at 390° C. The same catalyst achieved 54% yield of acrylic acid, 14% yield of acetaldehyde, and 14% yield of propionic acid from lactic acid.

Prof. D. Miller's group at Michigan State University (MSU) published many papers on the dehydration of lactic acid or lactic acid esters to acrylic acid and 2,3-pentanedione, such as Gunter et al., J. Catalysis 148:252-260 (1994); and Tam et al., Ind. Eng. Chem. Res. 38:3873-3877 (1999). The best acrylic acid yields reported by the group were about 33% when lactic acid was dehydrated at 350° C. over low surface area and pore volume silica impregnated with NaOH. In the same experiment, the acetaldehyde yield was 14.7% and the propionic acid yield was 4.1%. Examples of other catalysts tested by the group were $Na_2SO_4$, NaCl, $Na_3PO_4$, $NaNO_3$, $Na_2SiO_3$, $Na_4P_2O_7$, $NaH_2PO_4$, $Na_2HPO_4$, $Na_2HAsO_4$, $NaC_3H_5O_3$, NaOH, CsCl, $Cs_2SO_4$, KOH, CsOH, and LiOH. In all cases, the above referenced catalysts were tested as individual components, not in mixtures. Finally, the group suggested that the yield to acrylic acid is improved and the yield to the side products is suppressed when the surface area of the silica support is low, reaction temperature is high, reaction pressure is low, and residence time of the reactants in the catalyst bed is short.

Finally, the Chinese patent application 200910054519.7 discloses the use of ZSM-5 molecular sieves modified with aqueous alkali (such as $NH_3$, NaOH, and $Na_2CO_3$) or a phosphoric acid salt (such as $NaH_2PO_4$, $Na_2HPO_4$, $LiH_2PO_4$, $LaPO_4$, etc.). The best yield of acrylic acid achieved in the dehydration of lactic acid was 83.9%, however that yield came at very long residence times.

Therefore, the manufacture of acrylic acid, acrylic acid derivatives, or mixtures thereof from lactic acid or lactate by processes, such as those described in the literature noted above, has demonstrated: 1) yields of acrylic acid, acrylic acid derivatives, or mixtures thereof not exceeding 70% at short residence times; 2) low selectivities of acrylic acid, acrylic acid derivatives, or mixtures thereof, i.e., significant amounts of undesired side products, such as acetaldehyde, 2,3-pentanedione, propionic acid, CO, and $CO_2$; 3) long residence times in the catalyst beds; and 4) catalyst deactivation in short time on stream (TOS). The side products can deposit onto the catalyst resulting in fouling, and premature and rapid deactivation of the catalyst. Further, once deposited, these side products can catalyze other undesired reactions, such as polymerization reactions. Aside from depositing on the catalysts, these side products, even when present in only small amounts, impose additional costs in processing acrylic acid (when present in the reaction product effluent) in the manufacture of SAP, for example. These deficiencies of the prior art processes and catalysts render them commercially non-viable.

Accordingly, there is a need for catalysts for the dehydration of lactic acid, lactic acid derivatives, or mixtures thereof to bio-based acrylic acid, acrylic acid derivatives, or mixtures thereof, with high yield, selectivity, and efficiency (i.e., short residence time), and high longevity catalysts.

SUMMARY OF THE INVENTION

A method of making acrylic acid, acrylic acid derivatives, or mixtures thereof is provided. The method comprises contacting a stream comprising lactic acid, lactic acid derivatives, or mixtures thereof with a bicomponent catalyst comprising an HO—Re(VII)=O moiety and a compound having an oxophilic metal.

Additional features of the invention may become apparent to those skilled in the art from a review of the following detailed description.

DETAILED DESCRIPTION OF THE INVENTION

I Definitions

As used herein, the term "bicomponent" catalyst refers to a catalyst with two or more components with catalytic activity.

As used herein, the term "bio-based" material refers to a renewable material.

As used herein, the term "renewable material" refers to a material that is produced from a renewable resource.

As used herein, the term "renewable resource" refers to a resource that is produced via a natural process at a rate comparable to its rate of consumption (e.g., within a 100 year time frame). The resource can be replenished naturally, or via agricultural techniques. Non-limiting examples of renewable resources include plants (e.g., sugar cane, beets, corn, potatoes, citrus fruit, woody plants, lignocellulose, hemicellulose, and cellulosic waste), animals, fish, bacteria, fungi, and forestry products. These resources can be naturally occurring, hybrids, or genetically engineered organisms. Natural resources, such as crude oil, coal, natural gas, and peat, which take longer than 100 years to form, are not considered renewable resources. Because at least part of the material of the invention is derived from a renewable resource, which can sequester carbon dioxide, use of the material can reduce global warming potential and fossil fuel consumption.

As used herein, the term "fossil-derived" material refers to a material that is produced from fossil material, such as petroleum, natural gas, coal, etc.

As used herein, the term "condensed phosphate" refers to any salts containing one or several P—O—P bonds generated by corner sharing of $PO_4$ tetrahedra.

As used herein, the term "monophosphate" or "orthophosphate" refers to any salt whose anionic entity, $[PO_4]^{3-}$, is composed of four oxygen atoms arranged in an almost regular tetrahedral array about a central phosphorus atom.

As used herein, the term "oligophosphate" refers to any polyphosphates that contain five or less $PO_4$ units.

As used herein, the term "polyphosphate" refers to any condensed phosphates containing linear P—O—P linkages by corner sharing of $PO_4$ tetrahedra leading to the formation of finite chains.

As used herein, the term "ultraphosphate" refers to any condensed phosphate where at least two $PO_4$ tetrahedra of the anionic entity share three of their corners with the adjacent ones.

As used herein, the term "heteropolyanion" refers to any anion with covalently bonded $XO_p$ and $YO_r$ polyhedra, and thus includes X—O—Y and possibly X—O—X and Y—O—Y bonds, wherein X and Y represent any atoms, and wherein p and r are any positive integers.

As used herein, the term "heteropolyphosphate" refers to any heteropolyanion, wherein X represents phosphorus (P) and Y represents any other atom.

As used herein, the term "phosphate adduct" refers to any compound with one or more phosphate anions and one or more non-phosphate anions that are not covalently linked.

As used herein, the terms "LA" refers to lactic acid, "AA" refers to acrylic acid, "AcH" refers to acetaldehyde, and "PA" refers to propionic acid.

As used herein, the term "conversion" of LA in mol % is defined as [(lactic acid, lactic acid derivatives, or mixtures thereof flow rate in (mol/min))−(lactic acid, lactic acid derivatives, or mixtures thereof flow rate out (mol/min))]/[(lactic acid, lactic acid derivatives, or mixtures thereof flow rate in (mol/min))]×100.

As used herein, the term "yield" of a product in mol % is defined as [product flow rate out (mol/min)/(lactic acid, lactic acid derivatives, or mixtures thereof flow rate in (mol/min))]×100.

As used herein, the term "selectivity" of a product in mol % is defined as [Yield/Conversion]×100.

As used herein, the term "particle span" refers to a statistical representation of a given particle sample and is equal to $(D_{v,0.90} - D_{v,0.10})/D_{v,0.50}$. The term "median particle size" or $D_{v,0.50}$ refers to the diameter of a particle below which 50% of the total volume of particles lies. Further, $D_{v,0.10}$ refers to the particle size that separates the particle sample at the 10% by volume fraction and $D_{v,0.90}$ is the particle size that separates the particle sample at the 90% by volume fraction.

As used herein, the term "Gas Hourly Space Velocity" or "GHSV" in $h^{-1}$ is defined as 60×[Total gas flow rate (mL/min)/catalyst bed volume (mL)]. The total gas flow rate is calculated under Standard Temperature and Pressure conditions (STP; 0° C. and 1 atm).

As used herein, the term "Liquid Hourly Space Velocity" or "LHSV" in $h^{-1}$ is defined as 60×[Total liquid flow rate (ml/min)/catalyst bed volume (mL)].

II Catalysts for the Conversion of Lactic Acid, Lactic Acid Derivatives, or Mixtures Thereof Bicomponent catalysts containing the moiety HO—Re(VII)=O and a compound having an oxophilic metal dehydrate lactic acid, lactic acid derivatives, or mixtures thereof with high: 1) yield and selectivity for acrylic acid, acrylic acid derivatives, or mixtures thereof, i.e., low amount and few side products; 2) efficiency, i.e., performance in short residence time; and 3) longevity. Although not wishing to be bound by any theory, applicants believe that the moiety HO—Re(VII)=O reduces the activation energy for the dehydration reaction of lactic acid, lactic acid derivatives, or mixtures thereof because: 1) the moiety is a stronger Brønsted acid than lactic acid and 2) the spacing between the oxygen atom in the OH— group in the moiety and the basic O═atom in the moiety (about 2.65 Å) is very close to the spacing between the oxygen atom in the —OH group and the hydrogen atom in the $CH_3$ group in the lactic acid (about 2.66 Å; estimation of spacings was done using Jmol—an open-source Java viewer for chemical structures in 3D; http://www.jmol.org/). The lower activation energy allows the dehydration reaction to proceed at acceptable rates at low temperatures and in either liquid or gas phase. Furthermore, when this moiety is combined with a compound having an oxophilic metal, it forms a bicomponent catalyst, which simultaneously: 1) blocks the decarbonylation reaction of lactic acid, lactic acid derivatives, or mixtures thereof by complexation of the oxophilic metal with both the —OH and carboxylate groups in lactic acid and/or lactic acid derivatives, and 2) catalyzes the dehydration reaction at low temperatures and in either the liquid or gas phase via the HO—Re(VII)═O moiety of the bicomponent catalyst.

In one embodiment of the present invention, the bicomponent catalyst includes an HO—Re(VII)═O moiety and a compound having an oxophilic metal. In another embodiment of the present invention, the HO—Re(VII)═O moiety comprises perrhenic acid.

In one embodiment of the present invention, the oxophilic metal is selected from the group consisting of Be, Mg, Ca, Sr, Ba, Sc, Y, lanthanides (i.e., Ce, Pr, Nd, Pm, Sm, Eu, Gd, Tb, Dy, Ho, Er, Tm, Yb, and Lu), actinides (i.e., Th, Pa, U, Np, Pu, Am, Cm, Bk, Cf, Es, Fm, Md, No, and Lr), Ti, Zr, Hf, Rf, V, Nb, Ta, Db, Cr, Mo, W, Sg, Mn, Tc, Re, and Bh. In another embodiment of the present invention, the oxophilic metal is selected from the group consisting of Mg, Ca, Sr, Ba, Y, Ti, Zr, Hf, V, Nb, Ta, Cr, Mo, and W. In yet another embodiment of the present invention, the oxophilic metal is selected from the group consisting of Mg, Ca, Sr, and Ba. In even yet another embodiment of the present invention, the oxophilic metal is Ba.

Non-limiting examples of a compound having an oxophilic metal are oxophilic metal phosphate, oxophilic metal condensed phosphate, oxophilic metal sulfate, oxophilic metal oxide, oxophilic metal arsenate, oxophilic metal condensed arsenate, oxophilic metal nitrate, oxophilic metal borate, oxophilic metal carbonate, oxophilic metal chromate, oxophilic metal vanadate, oxophilic metal niobate, oxophilic metal tantalate, oxophilic metal selenate, and other oxophilic metal monomeric oxyanion or polyoxoanion that may be apparent to those having ordinary skill in the art. Non-limiting examples of a compound having an oxophilic metal and a heteropolyanion are heteropolyphosphate, such as arsenatophosphate, phosphoaluminate, phosphoborate, phosphochromate, phosphomolybdate, phosphosilicate, phosphosulfate, phosphotungstate, and others that may be apparent to those having ordinary skill in the art.

In one embodiment of the present invention, the compound having an oxophilic metal is selected from the group consisting of oxophilic metal phosphate, oxophilic metal sulfate, oxophilic metal oxide, and mixtures thereof. In another embodiment of the present invention, the phosphate in the oxophilic metal phosphate is selected from the group consisting of monophosphate, condensed phosphate, oligophosphate, polyphosphate, cyclophosphate, ultraphosphate, and mixtures thereof. In yet another embodiment of the present invention, the phosphate in the oxophilic metal phosphate is selected from the group consisting of polyphosphate, cyclophosphate, ultraphosphate, and mixtures thereof. In even yet another embodiment of the present invention, the oxophilic metal phosphate is selected from the group consisting of $M_2P_2O_7$, $M_3(PO_4)_2$, $MHPO_4$, $M(H_2PO_4)_2$, and mixtures thereof, wherein M is selected from the group consisting of Be, Mg, Ca, Sr, Ba, and mixtures thereof.

In one embodiment of the present invention, the oxophilic metal oxide is selected from the group consisting of $Nb_2O_5$, $LiONbO_2$, $Ta_2O_5$, and mixtures thereof.

The bicomponent catalyst can include an inert support (also called carrier) that is constructed of a material comprising silicates, aluminates, carbons, metal oxides, and mixtures thereof. Alternatively, the carrier is inert relative to the reaction mixture expected to contact the bicomponent catalyst. In the context of the reactions expressly described herein, in one embodiment of the present invention, the carrier is a low surface area silica or zirconia. When present, the carrier represents an amount of about 5 wt % to about 98 wt %, based on the total weight of the bicomponent catalyst. Generally, a bicomponent catalyst that includes an inert support can be made by one of two exemplary methods: impregnation or co-precipitation. In the impregnation method, a suspension of the solid inert support is treated with a solution of a pre-catalyst, and the resulting material is then activated under conditions that will convert the pre-catalyst to a more active state. In the co-precipitation method, a homogenous solution of the catalyst ingredients is precipitated by the addition of additional ingredients.

In one embodiment of the present invention, the bicomponent catalyst is calcined. Calcination is a process that allows chemical reaction and/or thermal decomposition and/or phase transition and/or removal of volatile materials. The calcination process is carried out with any equipment known to those skilled in the art, such as, by way of example and not limitation, furnaces or reactors of various designs, including shaft furnaces, rotary kilns, hearth furnaces, and fluidized bed reactors. The calcination temperature is, in one embodiment of the present invention, about 200° C. to about 1200° C.; in another embodiment of the present invention, the calcination temperature is about 250° C. to about 900° C.; in yet another embodiment of the present invention, the calcination temperature is about 450° C. to about 650° C.; and in even yet another embodiment of the present invention, the calcination temperature is about 300° C. to about 600° C. The calcination time is, in one embodiment of the present invention, about one hour to about seventy-two hours. In another embodiment, the calcination time is between about two hours and about twelve hours. In yet another embodiment, the calcination time is about four hours. In one embodiment, the heating ramp is about 0.5° C./min to about 20° C./min. In another embodiment, the heating ramp is about 10° C./min.

While many methods and machines are known to those skilled in the art for fractionating particles into discreet sizes and determining particle size distribution, sieving is one of the easiest, least expensive, and common ways. An alternative way to determine the size distribution of particles is with light scattering. Following calcination, the bicomponent catalyst is, in one embodiment of the present invention, ground and sieved to provide a more uniform product. The particle size distribution of the bicomponent catalyst particles includes a particle span that, in one embodiment of the present invention, is less than about 3; in another embodiment of the present invention, the particle size distribution of the bicomponent catalyst particles includes a particle span that is less than about 2; and in yet another embodiment of the present invention, the particle size distribution of the bicomponent catalyst particles includes a particle span that is less than about 1.5. In another embodiment of the present invention, the bicomponent catalyst is sieved to a median particle size of about 50 μm to about 500 μm. In another embodiment of the present invention, the bicomponent catalyst is sieved to a median particle size of about 100 μm to about 200 μm.

In one embodiment of the present invention, the method of preparing the bicomponent catalyst includes molding the catalyst particles. Non-limiting examples of molding operations are granulation, agglomeration, compaction, pelleting, and extrusion.

Following calcination and optional grinding and sieving, the bicomponent catalyst can be utilized to catalyze several chemical reactions. Non-limiting examples of reactions are: dehydration of lactic acid to acrylic acid (as described in further detail below); dehydration of 3-hydroxypropionic acid or 3-hydroxypropionic acid derivatives, or mixtures thereof to acrylic acid; oxydehydration of glycerin to acrolein; isomerization of lactic acid to 3-hydroxypropionic acid in the presence of water; reduction of lactic acid to propanoic acid or 1-propanol in the presence of hydrogen gas, dehydration of aliphatic alcohols to alkenes or olefins; dehydration of ethanolamine to ethylenimine; dehydrogenation of aliphatic alcohols to ethers; dehydration of bicyclic ethers produced by the Diels-Alder reaction of a furan molecule with ethylene (e.g. 2,5-dimethylfuran (DMF) and ethylene produces 1,4-dimethyl-7-oxa-bicyclo[2,2,1]-hept-2-ene or 2,5-furandicarboxylic acid (FDCA) and ethylene produces 7-oxa-bicyclo[2.2.1]-hept-2-ene-1,4-dicarboxylic acid to produce substituted aromatics, e.g. para-xylene or terephthalic acid); other dehydrogenations, hydrolyses, alkylations, dealkylations, oxidations, disproportionations, esterifications, cyclizations, isomerizations, condensations, aromatizations, polymerizations; and other reactions that may be apparent to those having ordinary skill in the art.

III Methods of Producing Acrylic Acid, Acrylic Acid Derivatives, or Mixtures Thereof In one embodiment of the present invention, a method of making acrylic acid, acrylic acid derivatives, or mixtures thereof comprising contacting a stream comprising lactic acid, lactic acid derivatives, or mixtures thereof with any catalyst disclosed in Section II ("Catalysts for the Conversion of Lactic Acid, Lactic Acid Derivatives, or Mixtures Thereof") of the present invention is provided.

Lactic acid can be L-lactic acid, D-lactic acid, or mixtures thereof. Lactic acid derivatives can be metal or ammonium salts of lactic acid, alkyl esters of lactic acid, lactic acid oligomers, cyclic di-esters of lactic acid, lactic acid anhydride, 2-alkoxypropoanoic acids or their alkyl esters, 2-aryloxypropanoic acids or their alkyl esters, 2-acyloxypropanoic acids or their alkyl esters, or a mixture thereof. Non-limiting examples of metal salts of lactic acid are sodium lactate, potassium lactate, and calcium lactate. Non-limiting examples of alkyl esters of lactic acid are methyl lactate, ethyl lactate, butyl lactate, 2-ethylhexyl lactate, or mixtures thereof. A non-limiting example of cyclic di-esters of lactic acid is dilactide. Non-limiting examples of 2-alkoxypropoanoic acids are 2-methoxypropanoic acid and 2-ethoxypropanoic acid. A non-limiting example of 2-aryloxypropanoic acid is 2-phenoxypropanoic acid. A non-limiting example of 2-acyloxypropanoic acid is 2-acetoxypropanoic acid.

Acrylic acid derivatives can be metal or ammonium salts of acrylic acid, alkyl esters of acrylic acid, acrylic acid oligomers, or mixtures thereof. Non-limiting examples of metal salts of acrylic acid are sodium acrylate, potassium acrylate, and calcium acrylate. Non-limiting examples of alkyl esters of acrylic acid are methyl acrylate, ethyl acrylate, butyl acrylate, 2-ethylhexyl acrylate, or mixtures thereof.

In one embodiment of the present invention, the stream comprising lactic acid, lactic acid derivatives, or mixtures thereof is liquid. The liquid stream can include the lactic acid, lactic acid derivatives, or mixtures thereof and a diluent. Non-limiting examples of the diluent are water, methanol, ethanol, acetone, C3 to C8 linear and branched alcohols, C5 to C8 linear and branched alkanes, ethyl acetate, non-volatile ethers (including diphenyl ether), and mixtures thereof. In one embodiment of the present invention, the diluent comprises water. In another embodiment of the present invention, the liquid stream comprises an aqueous solution of lactic acid or lactic acid derivatives selected from the group consisting of lactide, lactic acid oligomers, salts of lactic acid, 2-alkoxypropanoic acids or their alkyl esters, 2-aryloxypropanoic acids or their alkyl esters, 2-acyloxypropanoic acids or their alkyl esters, and alkyl lactates.

In one embodiment of the present invention, the liquid stream includes between about 2 wt % to about 95 wt % lactic acid or lactic acid derivatives, based on the total weight of the liquid stream. In another embodiment of the present invention, the liquid steam includes between about 5 wt % to about 50 wt % lactic acid or lactic acid derivatives, based on the total weight of the liquid stream. In yet another embodiment of the present invention, the liquid stream includes between about 10 wt % to about 25 wt % lactic acid or lactic acid derivatives, based on the total weight of the liquid stream. In even yet another embodiment of the present invention, the liquid stream includes about 20 wt % lactic acid or lactic acid derivatives, based on the total weight of the liquid stream.

In one embodiment of the present invention, the liquid stream comprises an aqueous solution of lactic acid along with derivatives of lactic acid. In another embodiment of the present invention, the liquid stream comprises less than about 30 wt % of lactic acid derivatives, based on the total weight of the liquid stream. In yet another embodiment of the present invention, the liquid stream comprises less than about 10 wt % of lactic acid derivatives, based on the total weight of the liquid stream. In even yet another embodiment of the present invention, the liquid stream comprises less than about 5 wt % of lactic acid derivatives, based on the total weight of the liquid stream.

In one embodiment of the present invention, the stream comprising lactic acid, lactic acid derivatives, or mixtures thereof is gaseous. In another embodiment of the present invention, the stream comprising lactic acid, lactic acid derivatives, or mixtures thereof comprises a liquid stream and an inert gas, that can be separately or jointly fed into the reactor comprising the bicomponent catalyst. The inert gas is a gas that is otherwise inert to the reaction mixture under the conditions of the method. Non-limiting examples of the inert gas are nitrogen, air, helium, argon, carbon dioxide, carbon monoxide, steam, and mixtures thereof. In one embodiment of the present invention, the inert gas is nitrogen.

In one embodiment of the present invention, the concentration of lactic acid, lactic acid derivatives, or mixtures thereof based on the total moles of the gaseous stream (calculated under STP conditions) is between about 0.5 mol % to about 50 mol %. In another embodiment of the present invention, the concentration of lactic acid, lactic acid derivatives, or mixtures thereof based on the total moles of the gaseous stream (calculated under STP conditions) is between about 1 mol % to about 10 mol %. In yet another embodiment of the present invention, the concentration of lactic acid, lactic acid derivatives, or mixtures thereof based on the total moles of the gaseous stream (calculated under STP conditions) is between about 1.5 mol % to about 3.5 mol %. In even yet another embodiment of the present invention, the concentration of lactic acid, lactic acid derivatives, or mixtures thereof based on the total moles of the gaseous stream (calculated under STP conditions) is about 2.5 mol %.

In one embodiment of the present invention, the contacting of the stream comprising lactic acid, lactic acid derivatives, or mixtures thereof with the bicomponent catalyst is carried out at a temperature between about 80° C. and about 700° C. In another embodiment of the present invention, the contacting of the stream comprising lactic acid, lactic acid derivatives, or mixtures thereof with the bicomponent catalyst is carried out at a temperature between about 100° C. and about 500° C. In yet another embodiment of the present invention, the contacting of the stream comprising lactic acid, lactic acid derivatives, or mixtures thereof with the bicomponent catalyst is carried out at a temperature between about 120° C. and about 400° C. In even yet another embodiment of the present invention, the contacting of the stream comprising lactic acid, lactic acid derivatives, or mixtures thereof with the bicomponent catalyst is carried out at a temperature between about 180° C. and about 250° C. In one embodiment of the present invention, the contacting of the stream comprising lactic acid, lactic acid derivatives, or mixtures thereof with the bicomponent catalyst is carried out at a temperature of about 200° C.

In one embodiment of the present invention, the stream comprising lactic acid, lactic acid derivatives, or mixtures thereof contacts the bicomponent catalyst at a GHSV between about 720 $h^{-1}$ and about 36,000 $h^{-1}$. In another embodiment of the present invention, the stream comprising lactic acid, lactic acid derivatives, or mixtures thereof contacts the bicomponent catalyst at a GHSV between about 1,800 $h^{-1}$ to about 7,200 $h^{-1}$. In yet another embodiment of the present invention, the stream comprising lactic acid, lactic acid derivatives, or mixtures thereof contacts the bicomponent catalyst at a GHSV of about 3,600 $h^{-1}$.

In one embodiment of the present invention, the stream comprising lactic acid, lactic acid derivatives, or mixtures thereof contacts the bicomponent catalyst at a pressure between about 0 psig and about 550 psig (37.9 barg). In another embodiment of the present invention, the stream comprising lactic acid, lactic acid derivatives, or mixtures thereof contacts the bicomponent catalyst at a pressure of about 360 psig (24.8 barg).

In one embodiment of the present invention, the diluent comprises water and the water partial pressure in the gaseous stream is about 10 psi (0.7 bar) or more. In another embodiment of the present invention, the diluent comprises water and the water partial pressure in the gaseous stream is between about 10 psi (0.7 bar) and about 500 psi (34.5 bar). In yet another embodiment of the present invention, the diluent comprises water and the water partial pressure in the gaseous stream is between about 15 psi (1 bar) and about 320 psi (22.1 bar). In even yet another embodiment of the present invention, the diluent comprises water and the water partial pressure in the gaseous stream is between about 50 psi (3.5 bar) and about 189 psi (13 bar). In one embodiment of the present invention, the diluent comprises water and the water partial pressure in the gaseous stream is about 189 psi (13 bar).

In one embodiment of the present invention, the stream comprising lactic acid, lactic acid derivatives, or mixtures thereof contacts the bicomponent catalyst in a reactor having an interior surface comprising material selected from the group consisting of quartz, borosilicate glass, silicon, manufactured sapphire, and mixtures thereof. In another embodiment of the present invention, the stream comprising lactic acid, lactic acid derivatives, or mixtures thereof contacts the bicomponent catalyst in a reactor having an interior surface comprising material selected from the group consisting of passivated hastelloy, passivated inconel, passivated stainless steel, and mixtures thereof. In yet another embodiment of the present invention, the stream comprising lactic acid, lactic acid derivatives, or mixtures thereof contacts the bicomponent catalyst in a reactor having an interior surface comprising material selected from the group consisting of quartz or borosilicate glass. In even yet another embodiment of the present invention, the stream comprising lactic acid, lactic acid derivatives, or mixtures thereof contacts the bicomponent catalyst in a reactor having an interior surface comprising borosilicate glass.

In one embodiment of the present invention, the method includes contacting the bicomponent catalyst with a stream comprising lactic acid, lactic acid derivatives, or mixtures thereof under conditions sufficient to produce acrylic acid, acrylic acid derivatives, or mixtures thereof in a yield of at least 50%. In another embodiment of the present invention, the method includes contacting the bicomponent catalyst with a stream comprising lactic acid, lactic acid derivatives, or mixtures thereof under conditions are sufficient to produce acrylic acid, acrylic acid derivatives, or mixtures thereof in a yield of at least about 70%. In yet another embodiment of the present invention, the method includes contacting the bicomponent catalyst with a stream comprising lactic acid, lactic acid derivatives, or mixtures thereof under conditions are sufficient to produce acrylic acid, acrylic acid derivatives, or mixtures thereof in a yield of at least about 80%.

In one embodiment of the present invention, the method conditions are sufficient to produce acrylic acid, acrylic acid derivatives, or mixtures thereof with a selectivity of at least about 50%. In another embodiment of the present invention, the method conditions are sufficient to produce acrylic acid, acrylic acid derivatives, or mixtures thereof with a selectivity of at least about 80%. In another embodiment of the present invention, the method conditions are sufficient to produce acrylic acid, acrylic acid derivatives, or mixtures thereof with a selectivity of at least about 90%.

In one embodiment of the present invention, the method conditions are sufficient to produce acrylic acid, acrylic acid derivatives, or mixtures thereof with propanoic acid as an impurity, wherein the propanoic acid selectivity is less than about 5%. In another embodiment of the present invention, the method conditions are sufficient to produce acrylic acid, acrylic acid derivatives, or mixtures thereof with propanoic acid as an impurity, wherein the propanoic acid selectivity is less than about 1%.

In one embodiment of the present invention, the method conditions are sufficient to produce acrylic acid, acrylic acid derivatives, or mixtures thereof with a conversion of said lactic acid, lactic acid derivatives, or mixtures thereof of more than about 50%. In another embodiment of the present invention, the method conditions are sufficient to produce acrylic acid, acrylic acid derivatives, or mixtures thereof with a conversion of said lactic acid, lactic acid derivatives, or mixtures thereof of more than about 80%. In another embodiment of the present invention, the method conditions are sufficient to produce acrylic acid, acrylic acid derivatives, or mixtures thereof with a conversion of said lactic acid, lactic acid derivatives, or mixtures thereof of more than about 90%.

Among the benefits attainable by the foregoing embodiments is the low yield of side products. In one embodiment of the present invention, the conditions are sufficient to produce propionic acid in a yield of less than about 6% from lactic acid present in the stream. In another embodiment of the present invention, the conditions are sufficient to produce propionic acid in a yield of less than about 1%, from lactic acid present in the stream.

In one embodiment of the present invention, the conditions are sufficient to produce each of acetic acid, pyruvic acid, 1,2-propanediol, hydroxyacetone, 3-hydroxypropanoic acid, acrylic acid dimer, and 2,3-pentanedione in a yield of less than about 2% from lactic acid present in the stream. In another embodiment of the present invention, the conditions are sufficient to produce each of acetic acid, pyruvic acid, 1,2-propanediol, hydroxyacetone, 3-hydroxypropanoic acid, acrylic acid dimer, and 2,3-pentanedione in a yield of less than about 0.5%, from lactic acid present in the stream.

In one embodiment of the present invention, the conditions are sufficient to produce acetaldehyde in a yield of less than about 8% from lactic acid present in the stream. In another embodiment of the present invention, the conditions are sufficient to produce acetaldehyde in a yield of less than about 4% from lactic acid present in the stream. In yet another embodiment of the present invention, the conditions are sufficient to produce acetaldehyde in a yield of less than about 3%, from lactic acid present in the stream.

IV Process for the Production of Acrylic Acid, Acrylic Acid Derivatives, or Mixtures Thereof In one embodiment of the present invention, a process for converting lactic acid, lactic acid derivatives, or mixtures thereof to acrylic acid, acrylic acid derivatives, or mixtures thereof comprises the following steps: a) providing an aqueous solution comprising lactic acid, lactic acid derivatives, or mixtures thereof; b) combining the aqueous solution with an inert gas to form an aqueous solution/gas blend; c) evaporating the aqueous solution/gas blend to produce a gaseous mixture; and d) dehydrating the gaseous mixture by contacting the mixture with any bicomponent dehydration catalyst disclosed in Section II ("Catalysts for the Conversion of Lactic Acid, Lactic Acid Derivatives, or Mixtures Thereof") of the present invention.

In another embodiment of the preset invention, a process for converting lactic acid, lactic acid derivatives, or mixtures thereof to acrylic acid, acrylic acid derivatives, or mixtures thereof comprises the following steps: a) providing a stream comprising lactic acid, lactic acid derivatives, or mixtures thereof; b) heating the stream to form a heated stream; and d) dehydrating the heated stream by contacting it with any bicomponent dehydration catalyst disclosed in Section II ("Catalysts for the Conversion of Lactic Acid, Lactic Acid Derivatives, or Mixtures Thereof") of the present invention. In another embodiment of the present invention, the stream is liquid. In yet another embodiment of the present invention the stream is gaseous.

Lactic acid can be in monomeric form or as oligomers in the stream or aqueous solution comprising lactic acid, lactic acid derivatives, or mixtures thereof. In one embodiment of the present invention, the oligomers of the lactic acid in the aqueous solution or stream of lactic acid, lactic acid derivatives, or mixtures thereof are less than about 25 wt % based on the total amount of lactic acid, lactic acid derivatives, or mixtures thereof. In another embodiment of the present invention, the oligomers of the lactic acid in an aqueous solution or stream of lactic acid, lactic acid derivatives, or mixtures thereof are less than about 10 wt % based on the total amount of lactic acid, lactic acid derivatives, or mixtures thereof. In yet another embodiment of the present invention, the oligomers of the lactic acid in an aqueous solution or stream of lactic acid, lactic acid derivatives, or mixtures thereof are less than about 5 wt % based on the total amount of lactic acid, lactic acid derivatives, or mixtures thereof. In even yet another embodiment of the present invention, the lactic acid is in monomeric form in an aqueous solution or stream of lactic acid, lactic acid derivatives, or mixtures thereof. The process steps to remove the oligomers from the aqueous solution or stream can be purification or diluting with water and heating. In one embodiment of the present invention, the heating step can involve heating the aqueous solution or stream of lactic acid, lactic acid derivatives, or mixtures thereof at a temperature between about 50° C. to about 100° C. to remove the oligomers of the lactic acid. In another embodiment of the present invention, the heating step can involve heating the lactic acid aqueous solution or stream at a temperature between about 95° C. to about 100° C. to remove the oligomers of the lactic acid and produce a monomeric lactic acid aqueous solution comprising at least 95 wt % of lactic acid in monomeric form based on the total amount of lactic acid. In yet another embodiment of the present invention, an about 88 wt % lactic acid aqueous solution (e.g. from Purac Corp., Lincolnshire, Ill.) is diluted with water to form an about 20 wt % lactic acid aqueous solution and remove the ester impurities that are produced from the intermolecular condensation reaction. These esters can result in loss of product due to their high boiling point and oligomerization in the evaporating stage of the process. Additionally, these esters can cause coking, catalyst deactivation, and reactor plugging. As the water content decreases in the aqueous solution, the loss of feed material to the catalytic reaction, due to losses in the evaporating step, increases.

In one embodiment of the present invention, the liquid stream comprising lactic acid, lactic acid derivatives, or mixtures thereof is combined with an inert gas. The inert gas can be introduced to the evaporating step separately or in combination with the liquid stream. The liquid stream can be introduced with a simple tube or through atomization nozzles. Non-limiting examples of atomization nozzles include fan nozzles, pressure swirl atomizers, air blast atomizers, two-fluid atomizers, rotary atomizers, and supercritical carbon dioxide atomizers. In one embodiment of the present invention, the droplets of the liquid stream are less than about 500 in diameter. In another embodiment of the present invention, the droplets of the liquid stream are less than about 200 µm in diameter. In yet another embodiment of the present invention, the droplets of the liquid stream are less than about 100 µm in diameter.

In the evaporating step, the aqueous solution/gas blend is heated to give a gaseous mixture. In one embodiment of the present invention, the temperature during the evaporating step is between about 165° C. to about 450° C. In another embodiment of the present invention, the temperature during the evaporating step is between about 250° C. to about 375° C. In another embodiment of the present invention, the temperature during the evaporating step is between about 300° C. to about 375° C.

In one embodiment of the present invention, the gas hourly space velocity (GHSV) in the evaporating step is between about 720 h$^{-1}$ to 7,200 h$^{-1}$. In another embodiment of the present invention, the gas hourly space velocity (GHSV) in the evaporating step is between about 6,000 h$^{-1}$ to about 7,200 h$^{-1}$. In yet another embodiment of the present invention, the gas hourly space velocity (GHSV) in the evaporating step is between about 720 h$^{-1}$ to about 3,600 h$^{-1}$.

The evaporating step can be performed at either atmospheric pressure or higher pressure. In one embodiment of the present invention, the evaporating step is performed under a pressure between about 80 psig (5.5 barg) to about 550 psig (37.9 barg). In another embodiment of the present invention, the evaporating step is performed under a pressure between about 300 psig (20.7 barg) to about 400 psig (27.6 barg). In yet another embodiment of the present invention, the evaporating step is performed under a pressure between about 350 psig (24.1 barg) to about 375 psig (25.9 barg).

In one embodiment of the present invention, the gaseous mixture comprises between about 0.5 mol % to about 50 mol % lactic acid, lactic acid derivatives, or mixtures thereof. In another embodiment of the present invention, the gaseous mixture comprises between about 1 mol % to about 10 mol % lactic acid, lactic acid derivatives, or mixtures thereof. In yet another embodiment of the present invention, the gaseous mixture comprises between about 1.5 mol % to about 3.5 mol % lactic acid, lactic acid derivatives, or mixtures thereof. In even yet another embodiment of the present invention, the gaseous mixture comprises about 2.5 mol % lactic acid, lactic acid derivatives, or mixtures thereof.

The evaporating step can be performed in various types of equipment, such as, but not limited to, plate heat exchanger, empty flow reactor, and fixed bed flow reactor. Regardless of the type of the reactor, in one embodiment of the present invention, the reactor has an interior surface comprising material selected from the group consisting of quartz, borosilicate glass, silicon, manufactured sapphire, and mixtures thereof. In another embodiment of the present invention, the reactor has an interior surface comprising material selected from the group consisting of passivated hastelloy, passivated inconel, passivated stainless steel, and mixtures thereof. In one embodiment of the present invention, the reactor has an interior surface comprising material selected from the group consisting of quartz, borosilicate glass, silicon, and mixtures thereof. The evaporating step can be performed in a reactor with the aqueous solution flowing down, or flowing up, or flowing horizontally. In one embodiment of the present invention, the evaporating step is performed in a reactor with the aqueous solution flowing down. Also, the evaporating step can be done in a batch form.

The gaseous mixture from the evaporating step is converted to acrylic acid, acrylic acid derivatives, and mixture thereof by contact it with a bicomponent catalyst in the dehydrating step. In one embodiment of the present invention, the dehydrating step is performed in a reactor, wherein the reactor has an interior surface comprising material selected from the group consisting of quartz, borosilicate glass, silicon, manufactured sapphire, and mixtures thereof. In another embodiment of the present invention, the reactor has an interior surface comprising material selected from the group consisting of passivated hastelloy, passivated inconel, passivated stainless steel, and mixtures thereof. In yet another embodiment of the present invention, the dehydrating step is performed in a reactor, wherein the reactor has an interior surface comprising material selected from the group consisting of quartz, borosilicate glass, and mixtures thereof.

The dehydrating step can be performed in a reactor with the gaseous mixture flowing down, flowing up, or flowing horizontally. In one embodiment of the present invention, the dehydrating step is performed in a reactor with the gaseous mixture flowing down. Also, the dehydrating step can be done in a batch form.

In one embodiment of the present invention, the evaporating and dehydrating steps are combined in a single step. In another embodiment of the present invention, the evaporating and dehydrating steps are performed sequentially in a single reactor. In another embodiment of the present invention, the evaporating and dehydrating steps are performed sequentially in a tandem reactor.

In one embodiment of the present invention, the dehydration occurs in the liquid phase, at least partially. In another embodiment of the present invention, the dehydration occurs in the aqueous phase, at least partially. In one embodiment of the present invention, the liquid phase dehydration is carried out in an apparatus, which is pressurized to ensure that all major components are in the liquid phase. In yet another embodiment of the present invention, the liquid phase dehydration is carried out in an apparatus, which is operated at low temperature to ensure that all major components are in the liquid phase.

In even yet another embodiment of the present invention, the liquid phase comprises a solvent. Non-limiting examples of solvents are hydrocarbons, chlorinated hydrocarbons, fluorinated hydrocarbons, brominated hydrocarbons, esters, ethers, ketones, aldehydes, acids, alcohols, or mixtures thereof. The liquid-phase dehydration can be conducted by using various methods, known to those skilled in the art, such as, by way of example and not limitation, fixed bed reactor, single-stage stirred tank reactor, multi-stage stirred tank reactor, multi-stage distillation column, and combinations thereof. These methods may be conducted batch-wise or continuously.

In one embodiment of the present invention, the dehydration occurs in the liquid phase using any catalyst disclosed in Section II ("Catalysts for the Conversion of Lactic Acid or its Derivatives to Acrylic Acid or its Derivatives") of the present invention.

The foregoing description is given for clearness of understanding only, and no unnecessary limitations should be understood therefrom, as modifications within the scope of the invention may be apparent to those having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making acrylic acid, acrylic acid derivatives, or mixtures thereof comprising contacting a stream comprising lactic acid, lactic acid derivatives, or mixtures thereof with a bicomponent catalyst comprising perrhenic acid and a compound having an oxophilic metal, wherein said oxophilic metal is selected from the group consisting of Be, Mg, Ca, Sr, Ba, Sc, Y, lanthanides, actinides, Ti, Zr, Hf, Rf, V Nb, Ta, Db, Cr, Mo, W, Sg, Mn, Tc, Re, and Bh.

2. The method of claim 1, wherein said oxophilic metal is selected from the group consisting of Mg, Ca, Sr, Ba, Y, Ti, Zr, Hf, V, Nb, Ta, Cr, Mo, and W.

3. The method of claim 1, wherein said compound having an oxophilic metal is selected from the group consisting of oxophilic metal phosphate, oxophilic metal sulfate, oxophilic metal oxide, and mixtures thereof.

4. The method of claim 3, wherein said oxophilic metal phosphate is selected from the group consisting of $M_2P_2O_7$, $M_3(PO_4)_2$, $MHPO_4$, $M(H_2PO_4)_2$, and mixtures thereof; and wherein M is selected from the group consisting of Be, Mg, Ca, Sr, Ba, and mixtures thereof.

5. The method of claim 3, wherein said oxophilic metal oxide is selected from the group consisting of $Nb_2O_5$, $LiONbO_2$, $Ta_2O_5$, and mixtures thereof.

6. The method of claim 1, wherein said contacting is carried out at a temperature between about 180° C. and about 250° C.

7. The method of claim 6, wherein said temperature is about 200° C.

8. The method of claim 1, wherein said stream is gaseous.

9. The method of claim 1, wherein said stream is liquid.

10. The method of claim 1, wherein the conversion of said lactic acid, lactic acid derivatives, or mixtures thereof is at least about 50 mol %.

11. The method of claim 10, wherein said conversion is at least about 80 mol %.

12. The method of claim 11, wherein said conversion is at least about 90 mol %.

13. The method of claim 1, wherein the selectivity of said acrylic acid, acrylic acid derivatives, or mixtures thereof is at least about 50 mol %.

14. The method of claim 13, wherein said selectivity is at least about 80 mol %.

15. The method of claim 14, wherein said selectivity is at least about 90 mol %.

* * * * *